(12) United States Patent
Touma (10) Patent No.: US 10,190,989 B2
(45) Date of Patent: Jan. 29, 2019

(54) METHOD AND APPARATUS FOR INSPECTING APPEARANCE OF OBJECT USING IMAGES PICKED UP UNDER DIFFERENT LIGHT QUANTITIES

(71) Applicant: DENSO WAVE INCORPORATED, Chita-gun, Aichi-pref. (JP)

(72) Inventor: Hirota Touma, Chita-gun (JP)

(73) Assignee: DENSO WAVE INCORPORATED, Chita-gun, Aichi-pref. (JP)

( * ) Notice: Subject to any disclaimer, the term of this patent is extended or adjusted under 35 U.S.C. 154(b) by 271 days.

(21) Appl. No.: 14/490,048

(22) Filed: Sep. 18, 2014

(65) Prior Publication Data
US 2015/0077541 A1    Mar. 19, 2015

(30) Foreign Application Priority Data

Sep. 18, 2013   (JP) ................... 2013-192940

(51) Int. Cl.
*G01N 21/88*     (2006.01)
*G06T 7/00*      (2017.01)
*H04N 5/225*     (2006.01)

(52) U.S. Cl.
CPC ..... *G01N 21/8803* (2013.01); *G01N 21/8806* (2013.01); *G06T 7/001* (2013.01); *G06T 7/0008* (2013.01); *H04N 5/2256* (2013.01); *G01N 2021/8835* (2013.01); *G06T 2207/10004* (2013.01); *G06T 2207/10152* (2013.01); *G06T 2207/30164* (2013.01)

(58) Field of Classification Search
USPC ........................................... 348/131
See application file for complete search history.

(56) References Cited

U.S. PATENT DOCUMENTS

| | | | | |
|---|---|---|---|---|
| 5,229,856 A | * | 7/1993 | Koshiishi | H04N 5/2354 348/312 |
| 5,589,875 A | * | 12/1996 | Fujita | G03B 7/085 348/143 |
| 5,708,873 A | * | 1/1998 | Kobayashi | G03B 7/16 396/159 |

(Continued)

FOREIGN PATENT DOCUMENTS

| | | |
|---|---|---|
| CN | 1822644 A | 8/2006 |
| JP | S60-086454 A | 5/1985 |

(Continued)

*Primary Examiner* — Leron Beck
(74) *Attorney, Agent, or Firm* — Oliff PLC (57) ABSTRACT

A method and apparatus for inspecting an object is provided. By way of example, first and second images of the object obtained by using a camera and a lighting unit. The lighting unit and the camera is controlled so as to provide the first image picked up by the camera with a first quantity of light radiated from the lighting unit and the second image picked up by the camera with the second quantity of light radiated from the lighting unit. The first quantity of light is different from the second quantity of light. Differences between pixel values of the first image and pixel values of the second image are calculated. Then, it is determined whether the object has a non-defective appearance or a detective appearance, based on comparison between the differences and reference pixel values corresponding to the differences.

10 Claims, 7 Drawing Sheets

(56) References Cited

U.S. PATENT DOCUMENTS

| | | | | |
|---|---|---|---|---|
| 6,347,150 | B1* | 2/2002 | Hiroi | G06T 7/001 |
| | | | | 250/559.39 |
| 2003/0206593 | A1* | 11/2003 | Srinivasan | H04N 19/70 |
| | | | | 375/240.16 |
| 2005/0243175 | A1* | 11/2005 | Yamada | H04N 5/2354 |
| | | | | 348/207.1 |
| 2006/0192117 | A1* | 8/2006 | Miyai | H01J 37/265 |
| | | | | 250/310 |
| 2006/0245635 | A1* | 11/2006 | Ishikawa | G06K 9/036 |
| | | | | 382/149 |
| 2007/0019858 | A1* | 1/2007 | Shimura | G06T 7/001 |
| | | | | 382/149 |
| 2007/0177787 | A1* | 8/2007 | Maeda | G06T 7/001 |
| | | | | 382/141 |
| 2010/0027873 | A1 | 2/2010 | Kakuda | |
| 2011/0095781 | A1* | 4/2011 | Murakami | G01N 21/95684 |
| | | | | 324/763.01 |
| 2012/0026316 | A1* | 2/2012 | Nagahama | G01N 21/95607 |
| | | | | 348/92 |
| 2012/0320218 | A1* | 12/2012 | Mori | H04N 5/2256 |
| | | | | 348/164 |
| 2013/0022258 | A1* | 1/2013 | Lee | G06T 5/002 |
| | | | | 382/132 |
| 2014/0078498 | A1* | 3/2014 | Ikushima | G01N 21/88 |
| | | | | 356/237.1 |

FOREIGN PATENT DOCUMENTS

| | | |
|---|---|---|
| JP | S61-169749 A | 7/1986 |
| JP | H03-082941 A | 4/1991 |
| JP | A-2004-61310 | 2/2004 |

* cited by examiner

FIG.7A
DIFFERENCE WITH 10% LIGHT QUANTITY
(FIRST DIFFERENCE)

FIG.7B
DIFFERENCE WITH 100% LIGHT QUANTITY
(SECOND DIFFERENCE)

FIG.7C

METHOD AND APPARATUS FOR INSPECTING APPEARANCE OF OBJECT USING IMAGES PICKED UP UNDER DIFFERENT LIGHT QUANTITIES

CROSS-REFERENCE TO RELATED APPLICATION

This application is based on and claims the benefit of priority from earlier Japanese Patent Application No. 2013-192940 filed Sep. 18, 2013, the description of which is incorporated herein by reference.

BACKGROUND OF THE INVENTION

Technical Field of the Invention

The present invention relates to a method and apparatus for performing appearance inspection of an object on the basis of an image of the object optically picked up by a camera.

Related Art

According to a system of this sort based on conventional art, whether the appearance of a workpiece as an inspection object is non-defective or defective is determined by picking up an image of the inspection object with a CCD (charge-coupled device) camera and by comparing degree of defect of a small area to be targeted of the inspection object with a reference value (see Patent Literature JP-A-2004-061310).

The system disclosed in PLT JP-A-2004-061310 uses a light emitting diode for a specified wavelength as a light source and also uses a filter which is mounted to the camera to cut light having a wavelength other than the specified wavelength to thereby prevent entry of disturbance light. In this way, in order to prevent entry of disturbance light in the conventional art, the light source is limited and a filter is required to be mounted to the camera.

SUMMARY

Hence it is desired to provide an appearance inspection apparatus which is able to eliminate the influence of disturbance light, while enabling use of an optionally selected light source.

As one exemplary embodiment, there is provided an apparatus for inspecting an appearance of an object. The apparatus includes a lighting unit radiating light to an object, the lighting unit being of selectively adjusting an quality of the light to a first light quantity and a second light quantity different from the first light quantity; a camera optically imaging the object; a unit obtaining first and second images of the object using the camera, the obtaining unit controlling the lighting unit and the camera so as to provide the first image picked up by the camera with the first light quantity and the second image picked up by the camera with the second light quantity; a unit calculating differences between pixel values of the first image and pixel values of the second image; and a unit determining whether the object has a non-defective appearance or a detective appearance based on comparison between the differences and reference pixel values corresponding to the differences.

Also as another exemplary embodiment, there is provided a method of inspecting an appearance of an object, comprising steps of: obtaining first and second images of an object using a camera and a lighting unit, the obtaining step including a step of controlling the lighting unit and the camera so as to provide the first image picked up by the camera with a first quantity of light radiated from the lighting unit and the second image picked up by the camera with the second quantity of light radiated from the lighting unit, the first quantity of light being different from the second quantity of light; calculating differences between pixel values of the first image and pixel values of the second image; and determining whether the object has a non-defective appearance or a detective appearance based on comparison between the differences and reference pixel values corresponding to the differences.

According to the above apparatus and method configurations, a difference between the pixel values of the first image of an object and the pixel values of the second image of the object is calculated. In this case, the first image is picked up by the camera by radiating light of the first light quantity using the lighting unit, while the second image is picked up by the camera by radiating light of the second light quantity using the lighting unit.

When disturbance light is radiated to an object, the pixel values caused by the disturbance light are equally or substantially equally superposed in the first and second images. The disturbance light is defined as light whose wavelengths are, at least partly, different from the wavelength range of the light radiated by the lighting unit, and includes illuminating light in the room, light reflected in the room and natural light. Accordingly, by calculating the difference in between the first and second images, the influence of the disturbance light can be eliminated. On the other hand, if the object has defects, such as cuts or taints, whose pixel values depend on the light quantity, the pixel values of the defective portions are left in the above difference.

Then, it is determined whether the appearance of the object is non-defective or defective (hereinafter the determination is referred to as non-defective/defective determination) on the basis of the comparison of the reference pixel values corresponding to the above difference, with the above difference. Accordingly, by comparing the pixel vales of the defective portions that have been left in the above difference with the reference pixel values, a non-defective/defective determination on the appearance of the object can be properly made. Thus, the influence of the disturbance light can be eliminated without using a combination such as of a light emitting diode and a filter, thereby enabling use of an optionally selected light source.

It is preferred that the reference pixel values are set as difference pixel values between pixel values of a third image and pixel values of a fourth image, the third image being picked up by the camera with the first light quantity, the fourth image being picked up by the cameral with the second light quantity.

According to the above configuration, the difference between the pixel values of the third image of a non-defective object (i.e., a reference object) and the pixel values of the fourth image of the non-defective object is used as reference pixel values. In this case, the third image is picked up by the camera by radiating light of the first light quantity using the lighting unit, and the fourth image is picked up by the camera by radiating light of the second light quantity using the lighting unit. The third image corresponds to the case where the object has no defects in the first image, while the fourth image corresponds to the case where the object has no defects in the second image. Thus, using the difference in pixel values between the third and fourth images as reference pixel values, appropriate reference pixel values can be set, which correspond to the difference in pixel values between the first and second images.

As another exemplary embodiment, there is provided an apparatus for inspecting an appearance of an object, comprising: a lighting unit radiating light to an object, the lighting unit being of selectively adjusting an quality of the light to a first light quantity and a second light quantity; a camera optically imaging the object, a unit obtaining first, second, third and fourth images using the camera, where the obtaining unit controlling the lighting unit and the camera so as to provide the first image of the object picked up by the camera with the first light quantity, the second image of the objet picked up by the camera with the second light quantity, the third image of a reference object with no detect picked up by the camera with the first light quantity, and the fourth image of the reference object with no detect picked up by the camera with the second light quantity; a unit calculating, pixel by pixel, as a first difference, a difference between pixel values of the first and third images and calculating, pixel by pixel, a second difference, a difference between pixel values of the second and fourth images; and a unit determining whether the object has a non-defective appearance or a detective appearance based on comparison between the first and second differences.

According to the above configuration, the first difference is calculated which is a difference between the pixel values of the first image of an object and the pixel values of the third image of a non-defective object. In this case, the first image of the object is picked up by the camera by radiating light with the first light quantity using the lighting unit, while the third image of the non-defective object is picked up by the camera by radiating the light with the first light quantity using the lighting unit. The first difference corresponds to a sum of the pixel values caused by disturbance light and defective portions in the image picked up with the first light quantity. Further, the second difference is calculated which is a difference between the pixel values of the second image of the object and the pixel values of the fourth image of the non-defective object. In this case, the second image of the object is picked up by the camera by radiating light with the second light quantity using the lighting unit, while the fourth image of the non-defective object is picked up by the camera by radiating the light with the second light quantity using the lighting unit. The second difference corresponds to a sum of the pixel values caused by disturbance light and defective portions in the image picked up with the second light quantity.

When disturbance light is radiated to an object, the pixel values caused by the disturbance light are equally or substantially equally superposed in the first and second images. On the other hand, if the object has defects whose pixel values depend on light quantity, the superposed pixel values of the defective portions are different between the first and second images. Accordingly, the disturbance light does not appear as a difference in pixel values between the first and second differences, whereas the defective portions appear as a difference in pixel values therebetween.

Then, based on the comparison between the first and second differences, a non-defective/defective determination is performed on the appearance of the object. Accordingly, based on the difference in pixel values caused by the defective portions, a non-defective/defective determination on the appearance of the object can be properly made. Thus, the influence of the disturbance light can be eliminated without using a combination such as of a light emitting diode and a filter, thereby enabling use of an optionally selected light source.

DETAILED DESCRIPTION OF THE PREFERRED EMBODIMENTS

With reference to the accompanying drawings, hereinafter are described some embodiments to which a workpiece appearance inspection apparatus of the present invention is applied.

(First Embodiment)

Referring first to FIGS. 1 to 5C, an appearance inspection apparatus according to a first embodiment of the present invention is described. The appearance inspection apparatus of the present embodiment is set up, for example, in an assembly line of a machine assembly factory.

Figure 1:
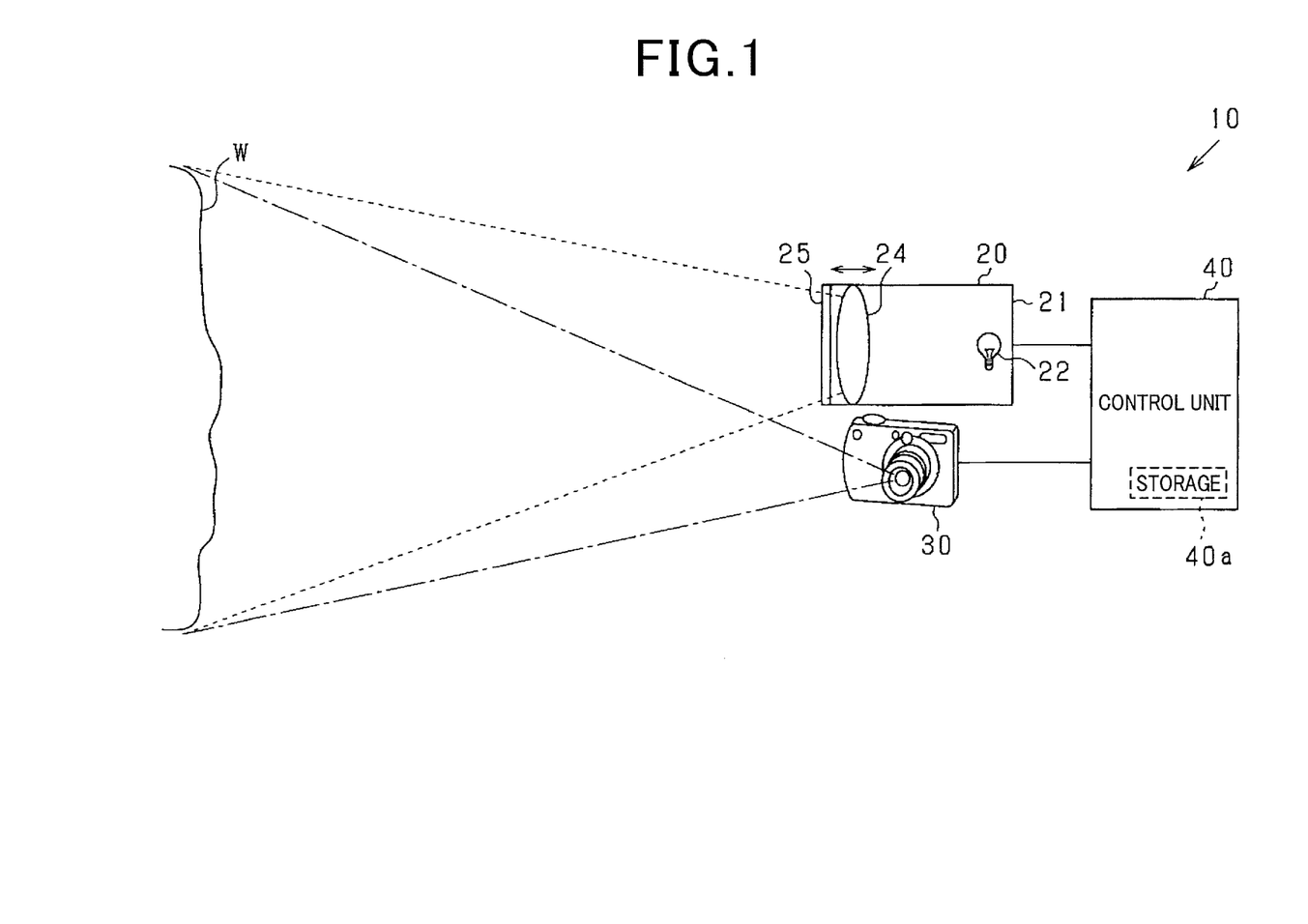
FIG. 1 is a schematic diagram illustrating an appearance inspection apparatus of the present invention.

FIG. 1 is a schematic diagram illustrating an appearance inspection apparatus 10 according to the first embodiment. The appearance inspection apparatus 10 includes a stroboscope 20, a camera 30 and a control unit 40.

The stroboscope 20 (lighting unit) is mounted to the camera 30 and includes, for example, a body 21, a lamp 22, a lens section 24 and a cover 25. The body 21 is formed into a hollow rectangular parallelepiped shape. The body 21 has an interior in which the lamp 22 and the lens section 24 are arranged. The body 21 has a front to which the cover 25, which is transparent, is mounted to transmit the light of the lamp 22.

The lamp 22 (light source) is configured such as by a xenon flash lamp to emit light to be applied to a workpiece W (i.e, an object being inspected). It should be noted that the lamp 22 may also be configured such as by a light emitting diode or an incandescent lamp. The on/off action of the lamp 22 and the light quantity in an on-state of the lamp 22 are controlled by the control unit 40. The lens section 24 collects and diffuses the light emitted from the lamp 22 to radiate the light in a direction of the cover 25. The focal point of the lens section 24 is automatically adjusted such that the light is radiated to a predetermined position of the workpiece W.

The camera 30 is a CCD camera, for example, which is able to pick up images in color. The camera 30 optically picks up an image of the workpiece W and acquires the image. The camera 30 is mounted to a hand (i.e., an end effector) of an arm of a robot, not shown. The arm of the robot has joints which are driven to change the position and direction of the arm. Further, with the change of the position and direction of the arm, the position and direction of the camera 30 are changed. Thus, the camera 30 can pick up an image of the workpiece W, which is conveyed to an inspection position such as by a belt conveyor, from any perspective. The image pick-up operation of the camera 30 is controlled by the control unit 40.

The control unit 40 includes a CPU, ROM, RAM, storage 40a, drive circuit, and position detection circuit. The ROM stores a system program, an operation program and the like of the robot. The RAM temporarily stores values of parameters, for example, in executing these programs. The storage 40a is a nonvolatile memory that stores data. The position detection circuit detects rotation angles of motors provided to the respective joints of the arm, on the basis of the detection signals of encoders which are provided to the respective joints. The CPU executes the operation program, which is given beforehand, to feedback-control the rotation angles of the joints of the arm for the achievement of respective target rotation angles, on the basis of the position information inputted from the position detection circuit.

In the present embodiment, as target position and direction of the arm, the control unit 40 determines in the appearance inspection of the workpiece W the position and direction of the arm (image pick-up position), which are used for the camera 30 to pick up an image of the workpiece W conveyed to the inspection position. The arm is driven to the image pick-up position so that the workpiece W that is in a state of being suitable for the inspection is caught in the field of view of the camera 30. An image of the workpiece W in this state is picked up by the camera 30 to thereby acquire an image of the workpiece W. Further, the control unit 40 controls the operation of the stroboscope 20 and the camera 30 to determine whether the appearance of the workpiece W is non-defective (acceptable) or defective (non-acceptable) (this determination is hereinafter referred to as non-defective/defective determination).

Figure 2:
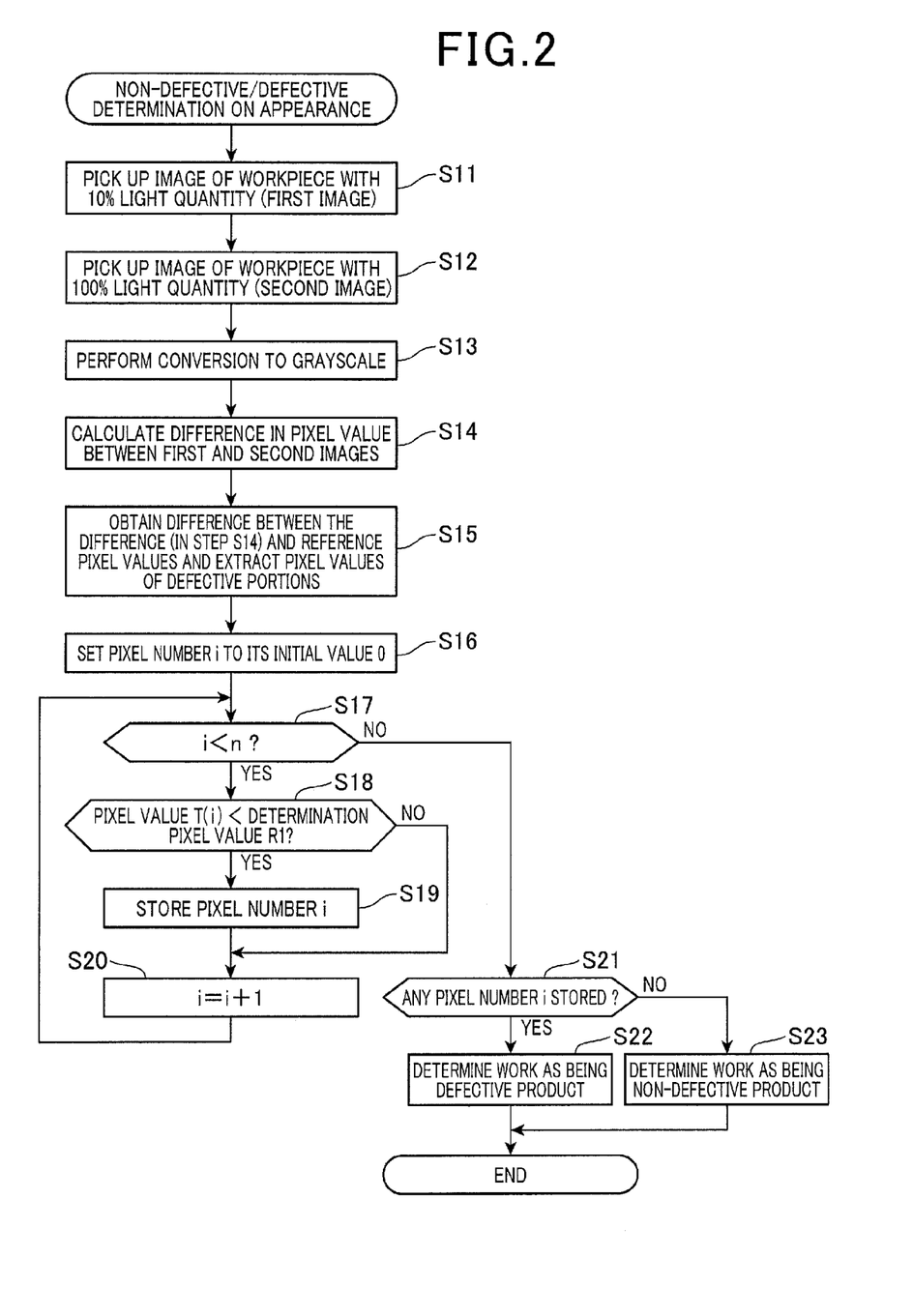
FIG. 2 is a flow diagram illustrating a process of non-defective/defective determination on the appearance of a workpiece, according to a first embodiment of the present invention.

FIG. 2 is a flow diagram illustrating a process of non-defective/defective determination on the appearance of the workpiece W. A series of steps of this process is performed by the control unit 40 during a continuous motion of the robot in the course of the appearance inspection.

First, the stroboscope 20 is lit up with a light quantity (first light quantity) of 10% of its maximum light quantity (100%) to input a first image that is an image of the workpiece W picked up in color by the camera 30 (step S11). Further, the stroboscope 20 is lit up with a light quantity (second light quantity) of 100% (i.e., its maximum output power or rating) to input a second image that is an image of the workpiece W picked up in color by the camera 30 (step S12). It should be noted that either of steps S11 and S12 may be performed first.

Then, the first and second images are each converted to a grayscale image (step S13). Specifically, using, for example, a simple average method, an intermediate value method or a G channel method, the color images are converted to grayscale images. The first and second images that have been converted to grayscale images are used on and after step S13.

Then, for each pixel, the control unit 40 calculates a difference (i.e., a two-dimensional difference image) between the pixel value of the first image and the pixel value of the second image (step S14). Specifically, the value (pixel value or pixel intensity) of each of the pixels can have a gradation of binarized values of from 0 (black) to 255 (white). In the first and second images, the pixels that have imaged the same position of the workpiece W are specified. Then, the pixel value of the first image is subtracted from the pixel value of the second image to calculate a difference at a specified pixel. This is repeated so that, at all the pixels, differences between the pixel values of the first image and the pixel values of the second image can be calculated.

Then, in respect of each pixel, the control unit 40 calculates a difference between the calculated difference (i.e., the two-dimensional difference image) and a reference pixel value (i.e., a reference image whose pixel values can be used as references), and extracts pixel values T caused by defects (i.e., defective portions), such as cuts and taints (hereinafter this pixel values are referred to as pixel values of a detect (or defective portion) T) (step S15). Specifically, for the calculated differences of all the pixels, respective reference pixel values are set. The reference pixel values will be explained later.

Subsequently, the control unit 40 sets a pixel number i for specifying pixels in the images to an initial value 0 (step S16). Specifically, the pixels of the images are numbered from 0 to n, with an initial pixel being numbered as 0. Then, it is determined whether or not the present pixel number i is smaller than n (step S17). The number n is the number of pixels.

In the above determination, if the present pixel number i is determined to be smaller than n (YES at step S17), the control unit 40 then determines whether or not the pixel value of a detective portion, T(i), at the pixel number i is smaller than a determination pixel value R1 (step S18). The determination pixel value R1 is set to a value that can determine defective portions of the workpiece W. For example, the determination pixel value R1 is set to a value that is a negative value of the 51-th pixel value (, which is denoted as "−51" pixel value) corresponding to 20% of the gradation consisting of 256 pixel values.

In the above determination, if the pixel value of the detective portion, T(i), at the pixel number i is determined to be smaller than the determination pixel value R1 (YES at step S18), the present pixel number i is stored in a predetermined region of the RAM (step S19). Then, the pixel number i is incremented by 1 to use the number as a new pixel number i (step S20). After that, the steps from step S17 onward are performed all over again. On the other hand, in the above determination, if he pixel value of the detective portion, T(i), at the pixel number i is determined not to be smaller than the determination pixel value R1 (NO at step S18), step S20 is performed.

Further, in the determination at step S17, if the present pixel number i is determined not to be smaller than n (NO at step S17), the control unit 40 determines whether or not there is a pixel number i stored in the predetermined region of the RAM (step S21). In other words, the control unit 40 determines whether or not there is a pixel number i whose pixel value of the detective portion, T(i), became smaller than the determination pixel value R1.

In the above determination, if it is determined that there is a pixel number i stored in the predetermined region of the RAM (YES at step S21), the control unit 40 determines that the workpiece W currently inspected is defective (step S22). On the other hand, in the above determination, if it is determined that there is no pixel number i stored in the predetermined region of the RAM (NO at step S21), the control unit 40 determines that the workpiece W currently inspected is non-defective (step S23). Then, the series of steps is halted until the next iteration (return). It should be noted that, when the appearance inspection is continuously performed for a plurality of workpieces W in the same shape, the steps from step S11 onward are performed all over again.

Figure 3A:
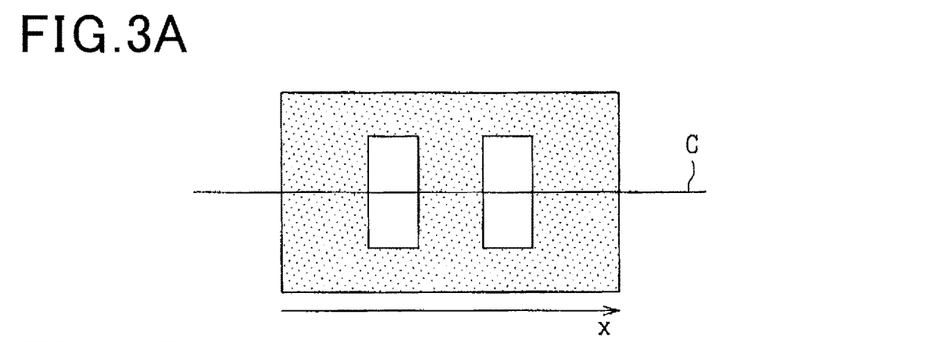
FIGS. 3A to 3C are diagrams illustrating a grayscale image and pixel values depending on light quantities in respect of a non-defective workpiece, according to the first embodiment.
Figure 3B:
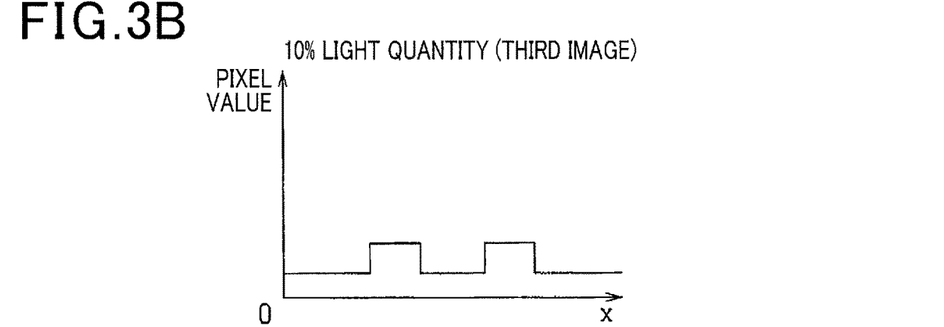
Figure 3C:
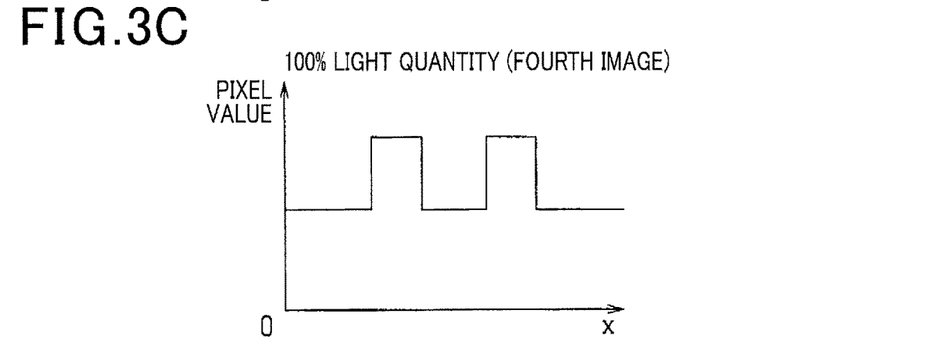

Hereinafter is described a grayscale image in respect of a to non-defective workpiece W having a correlation to values of pixels in the images, which pixel values (or pixel intensities) depend on light quantities. FIG. 3A is a grayscale image of the non-defective workpiece (i.e., a reference workpiece) W. FIG. 3B is a graph illustrating values (on the intensities) of pixels on a straight line C of FIG. 3A in the case where the light emitted from the stroboscope 20 has a light quantity of 10% of its maximum light quantity. FIG. 3C is a graph illustrating values of pixels on the straight line C of FIG. 3A in the case where the light emitted from the stroboscope 20 has a light quantity of 100%, i.e., its maximum light quantity.

Comparing FIG. 3B with FIG. 3C, the pixel values in the 10% light quantity are generally lower than the pixel values in the 100% light quantity. Specifically, in the portions having less reflection from the workpiece W (hatched portions in FIG. 3A), the pixel values in the 10% light quantity is lower than that in the 100% light quantity. Further, in the portions having more reflection from the workpiece W (non-hatched portions in FIG. 3A), the pixel values in the 10% light quantity are lower than that in the 100% light quantity. The difference in pixel values of the less-reflection portions from the more-reflection portions is smaller in the case of the 10% light quantity than in the case of the 100% light quantity. Further, the positions of the more-reflection portions in the x-direction coincide between the cases of the 10% light quantity and the 100% light quantity.

Figure 4A:
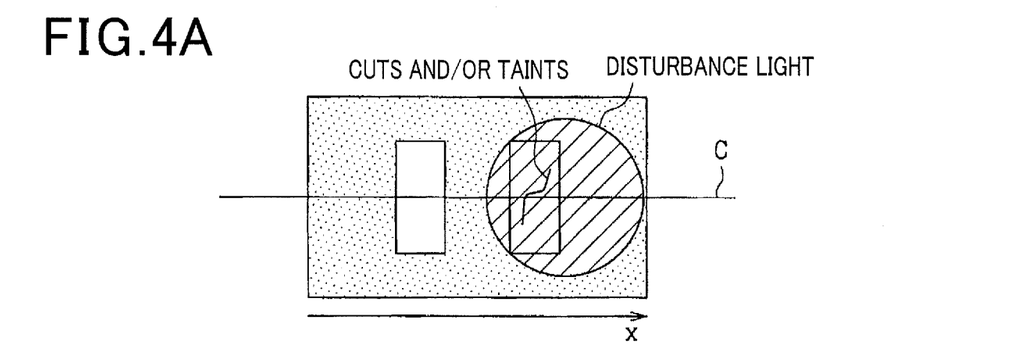
FIGS. 4A to 4C are diagrams illustrating a grayscale image and pixel values depending on light quantities in respect of a defective workpiece, according to the first embodiment.
Figure 4B:
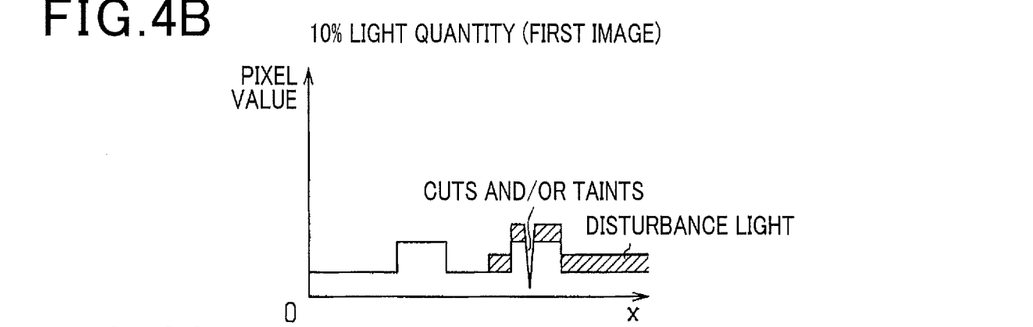
Figure 4C:
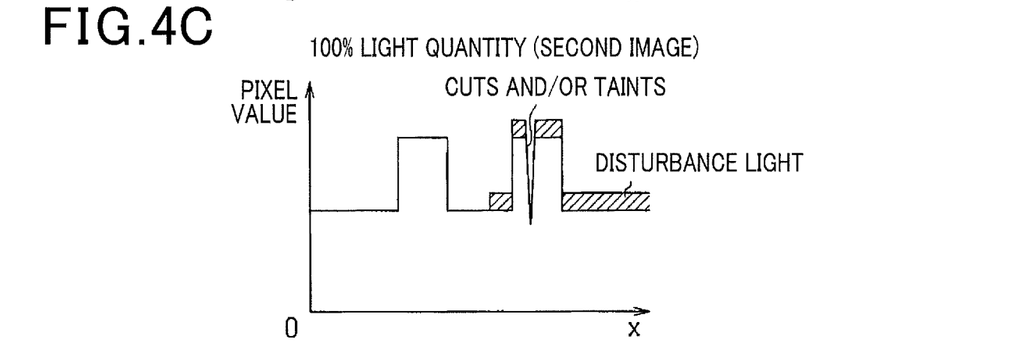

Hereinafter is described a grayscale image in respect of a defective workpiece W having a correlation to values (or intensities) of pixels in the images, which pixel values depend on light quantities. FIG. 4A is a grayscale image of the defective workpiece W. FIG. 4B is a graph illustrating values of pixels on a straight ling C of FIG. 4A in the case where the light emitted from the stroboscope 20 has a light quantity of 10%. FIG. 4C is a graph illustrating values of pixels on the straight ling C of FIG. 4A in the case where the light emitted from the stroboscope 20 has a light quantity of 100%. The image and pixel values shown in FIGS. 4A to 4C include disturbance light radiated to a part of the workpiece W. Incidentally, in the present embodiment, the disturbance light is defined as light whose wavelengths are, at least partly, different from the wavelength range of the light radiated by the stroboscope 20, and includes illuminating light in the room, light reflected in the room and natural light.

Comparing FIG. 4B with FIG. 4C, the pixel values in the 10% light quantity is generally lower than that in the 100% light quantity. This is similar to FIGS. 3A to 3C.

If the workpiece W has some cuts or taints, for example, the pixel values of the portions corresponding to these defects (i.e., defective portions) is lower than that in the portions having no defects. Specifically, the difference in pixel values of the portions with defects from the portions without defects is lower in the case of the 10% light quantity than in the case of the 100% light quantity. Further, the positions of the portions corresponding to the defective portions in the x-direction coincide between the cases of 10% light quantity and the 100% light quantity.

Further, in the case where disturbance light is radiated to the workpiece W, the pixel values in the portions radiated with the disturbance light is higher than in the portions where disturbance light is not radiated. Specifically, the pixel values superposed by the disturbance light is equal between the cases of the 10% light quantity and the 100% light quantity.

The influence of the disturbance light can be eliminated by calculating for each pixel a difference between the pixel value of the first image (FIG. 4B) and the pixel value of the second image (FIG. 4C). FIG. 5B is a graph showing a difference obtained by subtracting the graph of FIG. 4B from the graph of FIG. 4C. As shown in FIG. 5B, the pixel values caused by the disturbance light have been eliminated, while the pixel values caused by the defective portions have been left. Accordingly, a non-defective/defective determination on the appearance of the workpiece W can be made by comparing, pixel by pixel, the two-dimensional reference pixel values (that are pixel values of a reference image and are set based on experiments, for example, using a non-defective workpiece W) corresponding to the above difference, with the above difference.

However, where the pixel values of the first image of the object picked up with the 10% light quantity (first light quantity) have a small difference from the pixel values of the second image of the object picked up with the 100% light quantity (second light quantity), the difference in pixel values caused by the defective portions is small between the first and second images. Accordingly, in the difference in pixel values between the first and second images, the pixel values caused by the defective portions are likely to become unclear and thus there is a concern that the accuracy of determining the appearance of the workpiece W is impaired.

In this regard, when the 10% light quantity is used as the first light quantity, the pixel values (maximum gradation) of the first image picked up with the first light quantity has a value approximate to a minimum value. On the other hand, when the 100% light quantity is used as the second light quantity, the pixel values (maximum gradation) of the second image picked up with the second light quantity has a value approximate to a maximum value. Accordingly, the pixel values caused by the defective portions become clear and the accuracy of determining the appearance of the workpiece W is improved. Preferably, the first image uses, as the first light quantity, values of achieving pixel values corresponding to 0 to 30% of the gradation of binarized pixel values (, which are denoted as "0" to "77" pixel values), and the second image, for example, uses, as the second light quantity, values of achieving pixel values corresponding to 70 to 100% of the gradation of binarized pixel values (, which are denoted as "179" to "256" pixel values). Desirably, the first image uses, as the first light quantity, values of achieving pixel values corresponding to 0 to 20% of the gradation of binarized pixel values (, which are denoted as "0" to "51" pixel values), and the second image, for example, uses, as the second light quantity, values of achieving pixel values corresponding to 80 to 100% of the gradation of binarized pixel values (, which are denoted as "205" to "256" pixel values).

Figure 5A:
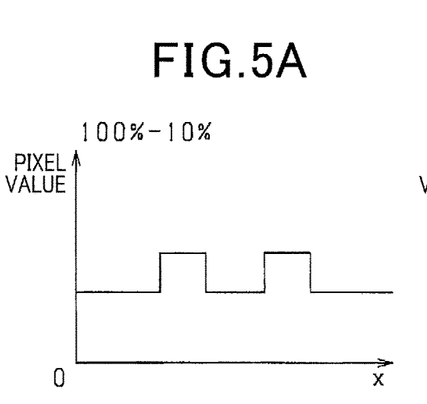
FIGS. 5A to 5C are graphs illustrating reference pixel values, difference pixel values and pixel values of a defective portion, respectively, according to the first embodiment.
Figure 5B:
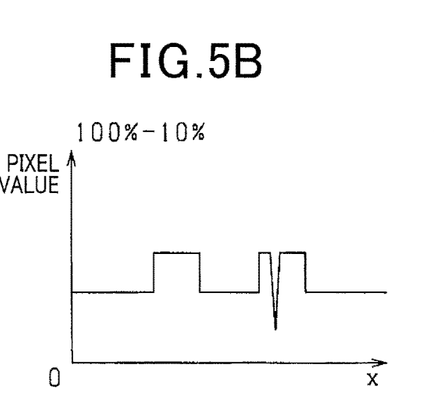

FIG. 5A is a graph showing a difference obtained by subtracting the graph of FIG. 3B from the graph of FIG. 3C. The graph shown in FIG. 5A corresponds to the case where defective portions shown in the graph of FIG. 5B are absent. Thus, the difference between the pixel values of the third image (grayscale image) of a non-defective workpiece W and the pixel values of the fourth image (grayscale image) of the non-defective workpiece W is used as the reference pixel values. In this case, the third image is picked up by the camera 30 by radiating the light of 10% light quantity using the stroboscope 20, while the fourth image is picked up by the camera 30 by radiating the light of 100% light quantity using the stroboscope 20. The reference pixel values are stored in the storage 40a of the control unit 40.

Figure 5C:
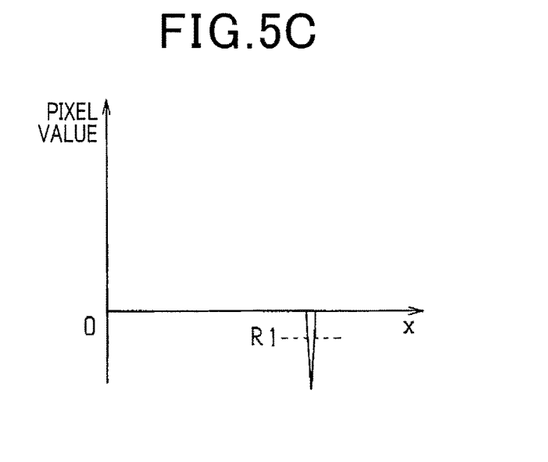

Further, by obtaining a difference between the difference shown in FIG. 5B and the reference pixel values shown in FIG. 5A, pixel values of a defective portion alone can be extracted as shown in FIG. 5C. Specifically, FIG. 5C is a graph that shows a difference obtained by subtracting the graph of FIG. 5A from the graph of FIG. 5B. Accordingly, when the pixel values of the defective portion, T, is determined to be lower than the determination pixel value R1 ("−51" pixel value), the workpiece W is determined to be a defective product.

The embodiment specifically described above has the following advantageous effects.

When disturbance light is radiated to the workpiece W, pixel values due to the disturbance light are equally or substantially equally superposed in both of the first image (FIG. 4B) and the second image (FIG. 4C). Accordingly, by calculating pixel by pixel differences between the pixel values of the first and second images, the influence of the disturbance light can be eliminated (see FIG. 5B). On the other hand, if the workpiece W has defects (i.e., defective portions), such as cuts or taints, the pixel values of the defective portions are left in the calculated differences mentioned above (see FIG. 5B), because the pixel values of the defective portions depend on the light quantity. Then, based on the comparison of the reference pixel values (FIG. 5A) corresponding to the differences, with the differences (FIG. 5B), the control unit 40 makes a non-defective/defective determination on the appearance of the workpiece W. Through the comparison of the pixel values of the defective portions left in the differences with the reference pixel values, a non-defective/defective determination on the appearance of the workpiece W can be properly made. Thus, the influence of the disturbance light can be eliminated without using a combination such as of a light emitting diode and a filter, thereby enabling use of an optionally selected light source.

The differences between the pixel values of the third image (FIG. 3B) of a non-defective workpiece W and the pixel values of the fourth image (FIG. 3C) of the non-defective workpiece W are used as the reference pixel values (see FIG. 5A). In this case, the third image is picked up by the camera 30 by radiating the light of 10% light quantity of its maximum light quantity using the stroboscope 20, while the fourth image is picked up by the camera 30 by radiating the light of 100% light quantity using the stroboscope 20. The third image corresponds to the case where defective portions of the workpiece W are absent from the first image. The fourth image corresponds to the case where defective portions of the workpiece W are absent from the second image. Accordingly, using the difference between the pixel values of the third and fourth images as the reference pixel values (i.e., the two-dimensional reference image), appropriate reference pixel values can be set, which correspond to the differences between the pixel values of the first and second images.

The control unit 40 obtains differences between the differences (FIG. 5B) and the reference pixel values (FIG. 5A) to extract pixel values of a defective portion of the workpiece W (FIG. 5C). Specifically, using the difference between the difference resulting from the elimination of the influence of the disturbance light and the reference pixel values, the pixel values of defective portions alone can be extracted. Then, based on the comparison between the pixel values of the defective portions and the determination pixel value R1, a non-defective/defective determination on the appearance of the workpiece W can be made. In this way, the appearance of the workpiece W can be correctly determined.

An image of the workpiece W is picked up twice with the 10% and 100% light quantities. However, the extension of time involved in picking up an image twice substantially causes no problem, when compared to the time required for the motion of the robot in the course of the appearance inspection.

(Second Embodiment)

Figure 6:
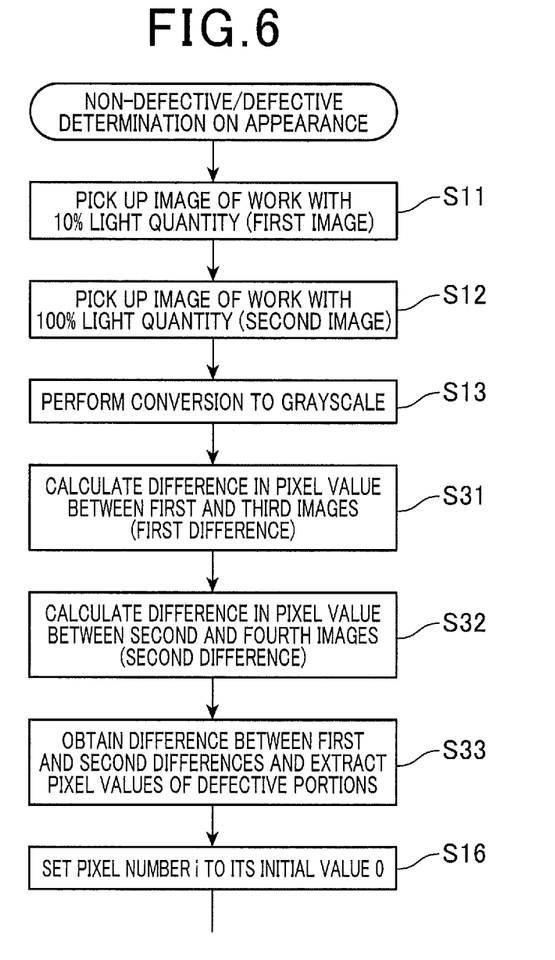
FIG. 6 is a flow diagram illustrating a process of non-defective/defective determination on the appearance of a workpiece, according to a second embodiment of the present invention.
Figure 7A:
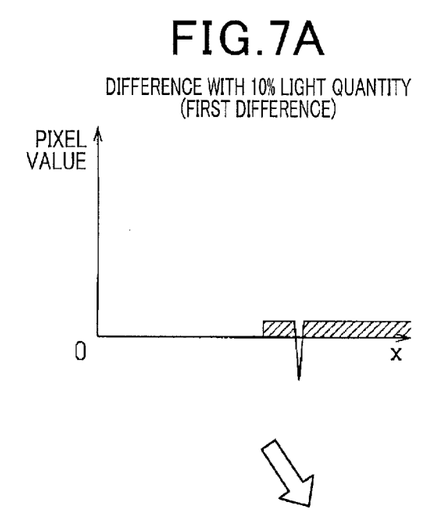
FIGS. 7A to 7C are graphs illustrating first difference pixel values, second difference pixel values and pixel values of a defective portion, respectively, according to the second embodiment.
Figure 7B:
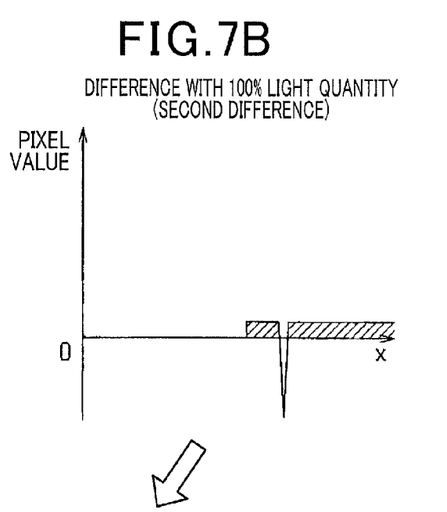
Figure 7C:
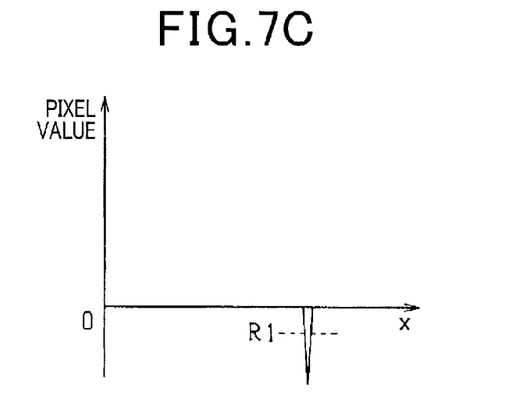

Referring to FIGS. 6 to 7C, a second embodiment of the present invention is described. In the second embodiment, the components and processing steps identical with or similar to those in the first embodiment are given the same reference numerals for the sake of omitting unnecessary explanation.

The second embodiment includes a modification in the non-defective/defective determination on the appearance of the workpiece W described above. FIG. 6 is a flow diagram illustrating a process of non-defective/defective determination on the appearance of the workpiece W.

After converting the first and second images to respective grayscale images at step S13, the control unit 40 calculates, for each pixel, a difference (first difference) between the pixel value of the first image and that of the third image (step S31). Specifically, the third image is obtained by picking up an image of a non-defective workpiece (i.e., a reference workpiece) W in advance by the camera 30 by radiating the light of 10% light quantity using the stroboscope 20, and converting the image to a grayscale image (FIG. 3B). Then, the pixels that have picked up an image of the same position of the workpiece W are specified in the first and third images. Then, at the specified pixel, the pixel value of the third image is subtracted from the pixel value of the first image to calculate a difference. Similarly, for all of the pixels, the differences in the pixel values between the first and third images are calculated.

Subsequently, for each pixel, a difference (second difference) in the pixel value between the second and fourth images is calculated (step S32). Specifically, the fourth image is obtained by picking up an image of a non-defective workpiece W in advance by the camera 30 by radiating the light of 100% light quantity using the stroboscope 20, and converting the image to a grayscale image (FIG. 3C). Then, the pixels that have been picked up an image of the same position of the workpiece W are specified in the second and fourth images. Then, at the the specified pixel, the pixel value of the fourth image is subtracted from the pixel value of the second image to calculate a difference. Similarly, for all of the pixels, the differences in the pixel values between the second and fourth images are calculated.

Subsequently, for each pixel, a difference between the calculated first and second differences is obtained, to extract pixel values of a defect, T, such as of cuts and taints of the workpiece W (step S33). Then, the steps on and after step S16 of FIG. 2 are performed.

FIGS. 7A, 7B and 7C are graphs showing the first difference, the second difference and pixel values of a defective portion, respectively.

Where the 10% light quantity is used, the difference between the pixel value of the first image (FIG. 4B) and that of the third image (FIG. 3B) is calculated for each pixel to eliminate the influence of making different the quantity of reflected light depending on the portions of the workpiece W. FIG. 7A is a graph showing a difference (first difference) obtained by subtracting the graph of FIG. 3B from the graph of FIG. 4B. The first difference corresponds to a sum of the pixel values of the disturbance light and the defective portions in the image picked up with the 10% light quantity. As shown in FIG. 7A, the pixel values caused by the portions of the workpiece W having no disturbance light and defective portions have been eliminated, while the pixel values caused by the disturbance light and defective portions has been left.

Similarly, where the 100% light quantity is used, the difference between the pixel value of the second image (FIG. 4C) and that of the fourth image (FIG. 3C) is calculated for each pixel to eliminate the influence of making different the quantity of reflected light depending on the portions of the workpiece W. FIG. 7B is a graph showing a difference (second difference) obtained by subtracting the graph of FIG. 3C from the graph of FIG. 4C. The second difference corresponds to a sum of the pixel values of the disturbance light and the defective portions in the image picked up with the 100% light quantity. As shown in FIG. 7B, the pixel values caused by the portions of the workpiece W having no disturbance light and defective portions has been eliminated, while the pixel values caused by the disturbance light and defective portions has been left.

Comparison between FIGS. 7A and 7B reveals that the difference in pixel values between the portions with defects and without defects is smaller in the case of using the 10% light quantity than in the case of using the 100% light quantity. Further, the pixel values superposed by the disturbance light is equal in the cases of using the 10% light quantity and the 100% light quantity. Thus, comparing the first and second differences, a non-defective/defective determination on the appearance of the workpiece W can be made.

Further, by obtaining a difference between the graph of the first difference shown in FIG. 7A and the graph of the second difference shown in FIG. 7B, the pixel values of the defect alone, as shown in FIG. 7C, can be extracted. Specifically, FIG. 7C is a graph showing a difference by subtracting the graph of FIG. 7A from the graph of FIG. 7B. Thus, when the pixel values of the defect, T, is determined to be lower than the determination pixel value R1 ("−51" pixel value), the workpiece W is determined to be a defective product.

The present embodiment specifically described above has the following advantageous effects.

When disturbance light is radiated to the workpiece W, pixel values are equally or substantially equally superposed by the disturbance light in the first image (FIG. 4B) and the second image (FIG. 4C). On the other hand, if the workpiece W has defects whose pixel values depend on the light quantity, the pixel values superposed by the defective portions are different between the first and second images. Accordingly, in the first difference (FIG. 7A) and the second difference (FIG. 7B), the disturbance light is not expressed as a difference in the pixel values, whereas the defects are expressed as a difference in the pixel values. Then, the control unit 40 compares the first and second differences, and based on the comparison, makes a non-defective/defective determination on the appearance of the workpiece W. Thus, based on the differences in pixel values caused by the defective portions, a non-defective/defective determination on the appearance of the workpiece W can be properly made. Accordingly, the influence of the disturbance light can be eliminated without using a combination such as of a light emitting diode and a filter, thereby enabling use of an optionally selected light source.

The control unit 40 obtains a difference between the first and second differences to extract pixel values of a defective portion of the workpiece W (see FIG. 7C). In other words, by obtaining a difference between the first and second differences that equally or substantially equally include the pixel values caused by the disturbance light, pixel values of a defective portion alone can be extracted, eliminating the influence of the disturbance light. Then, based on the comparison between the pixel values of the defective portion and the determination pixel value R1, a non-defective/defective determination on the appearance of the workpiece W is made, thereby enabling correct determination on the appearance of the workpiece W.

The embodiments described so far can also be modified and implemented as follows.

As the reference pixel values in the first embodiment, values used for correcting the third and fourth images in accord with the conditions, for example, of picking up the images can also be used, instead of the differences in the pixel values between the third and fourth images.

A camera for picking up black-and-white images can also be used as the camera 30. In this case, conversion to a grayscale image is not necessary. Accordingly, a non-defective/defective determination may be made by comparing the intensity of a pixel specified by the pixel number i in a black-and-white image, with the intensity of a pixel specified by the pixel number i in a reference image. Further, not only a CCD camera but also a camera using a CMOS sensor, for example, may be used as the camera 30.

The present invention described above is not limited by the above-described embodiments. The present invention can be applied to various other embodiments without departing from the spirit thereof.

What is claimed is:

1. An apparatus for inspecting an appearance of an object, comprising:
a lighting unit radiating light to an object being inspected, the lighting unit being capable of selectively adjusting a quantity of the light to a first light quantity and a second light quantity, the second light quantity being different from the first light quantity;
a camera optically imaging the object, the camera being fixed positionally; and
a control unit configured to
control the lighting unit and the camera so as to provide a first image picked up by the camera in a state where the light is selected to be of the first light quantity and is radiated to the object and a second image picked up by the camera in a state where the light is selected to be of the second light quantity and is radiated to the same object, each of the first and second images being composed of pixels having pixel values;
calculate differences, pixel by pixel, between the pixel values of the first image and the pixel values of the second image; and
determine whether the object has a non-defective appearance or a defective appearance based on a comparison between the calculated differences of the pixel values and reference pixel values which are set, pixel by pixel, as a reference for the determination, wherein the reference pixel values are set as difference pixel values between pixel values of a third image and pixel values of a fourth image, the third image being picked up by the camera in a state where the light is selected to be of the first light quantity and is radiated to a reference object which serves as a reference to the object being inspected, the fourth image being picked up by the camera in a state where the light is selected to be of the second light quantity and is radiated to the reference object.

2. The apparatus of claim 1, wherein
the control unit is configured to
extract pixel values of a defect of the object by calculating differences between the differences derived from the first and second images and the reference pixel values, and
determine whether or not the object has the non-defective appearance or the defective appearance based on a comparison between the pixel values of the defect and a determination pixel value.

3. The apparatus of claim 2, wherein
the first light quantity is lower than the second light quantity, and
the first light quantity is set to be a quantity of light whose wavelengths occupy a lower part of a predetermined gradation of pixel values, and the second light quantity is set to be a quantity of light whose wavelengths occupy a higher part of the predetermined gradation of pixel values, the higher part being higher than the lower part in the gradation.

4. An apparatus for inspecting an appearance of an object being inspected, comprising:
a lighting unit radiating light to an object, the lighting unit being of selectively adjusting a quantity of the light to a first light quantity and a second light quantity;
a camera optically imaging the object, the camera being fixed positionally, and
a control unit that
i) obtains first, second, third and fourth images using the camera, wherein the control unit controls the lighting unit and the camera so as to provide the first image of the object picked up by the camera in a state where the light is selected to be of the first light quantity, the second image of the object picked up by the camera in a state where the light is selected to be of the second light quantity, the third image as an image of a reference object with no detection picked up by the camera in a state where the light is selected to be of the first light quantity, and the fourth image as an image of the reference object picked up by the camera in a state where the light is selected to be of the second light quantity;
ii) calculates, pixel by pixel, as a first difference, a difference between pixel values of the first and third images and calculates, pixel by pixel, as a second difference, a difference between pixel values of the second and fourth images; and
iii) determines whether the object has a non-defective appearance or a defective appearance based on a comparison between the first difference and the second difference.

5. The apparatus of claim 4, wherein
the control unit is configured to
extract pixel values of a defect of the object by calculating a difference between the first and second differences; and
determine whether or not the object has the non-defective appearance or the defective appearance based on a comparison between the pixel values of the defect and a determination pixel value.

6. The apparatus of claim 5, wherein
the first light quantity is lower than the second light quantity.

7. The apparatus of claim 6, wherein the first light quantity is set to be a quantity of light whose wavelengths occupy a lower part of a predetermined gradation of pixel values, and the second light quantity is set to be a quantity of light whose wavelengths occupy a higher part of the predetermined gradation of pixel values, the higher part being higher than the lower part in the gradation.

8. The apparatus of claim 4, wherein the first light quantity is lower than the second light quantity.

9. The apparatus of claim 8, wherein the first light quantity is set to be a quantity of light whose wavelengths occupy a lower part of a predetermined gradation of pixel values, and the second light quantity is set to be a quantity of light whose wavelengths occupy a higher part of the predetermined gradation of pixel values, the higher part being higher than the lower part in the gradation.

10. A method of inspecting an appearance of an object being inspected, comprising the steps of:
obtaining first and second images of an object using an optical camera positionally fixed and a lighting unit, the obtaining step including a step of controlling both the lighting unit and the camera so as to provide the first image picked up by the camera in a state where a first quantity of light is radiated from the lighting unit to the object and the second image picked up by the camera in a state where a second quantity of light is radiated from the lighting unit to the same object, the first quantity of light being different from the second quantity of light, each of the first and second images being composed of pixels having pixel values;
calculating differences, pixel by pixel, between pixel values of the first image and pixel values of the second image; and
determining whether the object has a non-defective appearance or a defective appearance based on a comparison between the calculated differences of the pixel values and reference pixel values which are set, pixel by pixel, as a reference for the determination, to the calculated differences of the pixel values,
wherein the reference pixel values are set as difference pixel values between pixel values of a third image and pixel values of a fourth image, the third image being picked up by the camera in a state where the light is selected to be of the first light quantity and is radiated to a reference object which serves as a reference to the object being inspected, the fourth image being picked up by the camera in a state where the light is selected to be of the second light quantity and is radiated to the reference object.

* * * * *